United States Patent
Banfield et al.

(10) Patent No.: US 7,309,001 B2
(45) Date of Patent: Dec. 18, 2007

(54) SYSTEM TO PROVIDE SPECIFIC MESSAGES TO PATIENTS

(75) Inventors: Simon Banfield, Tierra Verde, FL (US); Edward E. Rhoads, New York, NY (US); Michael F. Roberts, Palm Harbor, FL (US)

(73) Assignee: Catalina Marketing Corporation, St. Petersburg, FL (US)

( * ) Notice: Subject to any disclaimer, the term of this patent is extended or adjusted under 35 U.S.C. 154(b) by 0 days.

(21) Appl. No.: 11/235,083

(22) Filed: Sep. 27, 2005

(65) Prior Publication Data

US 2006/0266826 A1 Nov. 30, 2006

Related U.S. Application Data

(60) Provisional application No. 60/685,491, filed on May 31, 2005.

(51) Int. Cl.
 *G06F 17/00* (2006.01)
(52) U.S. Cl. .................. 235/375; 235/381; 235/383
(58) Field of Classification Search ............... 235/375, 235/486, 380, 381, 383; 705/3
See application file for complete search history.

(56) References Cited

U.S. PATENT DOCUMENTS 6,202,923 B1 * 3/2001 Boyer et al. ............... 235/375
6,208,973 B1 * 3/2001 Boyer et al. ................. 705/2
6,240,394 B1   5/2001 Uecker et al.
6,732,113 B1 * 5/2004 Ober et al. ................ 707/102
6,836,843 B2  12/2004 Seroussi et al.
2002/0111833 A1 *  8/2002 Dick ............................. 705/3
2003/0229519 A1 * 12/2003 Eidex et al. .................. 705/2
2004/0143171 A1 *  7/2004 Kalies ........................ 600/300
2004/0143594 A1 *  7/2004 Kalies .................... 707/103 R
2004/0148195 A1 *  7/2004 Kalies ........................... 705/2
2004/0215981 A1   10/2004 Ricciardi et al.
2004/0256453 A1 * 12/2004 Lammle .................... 235/381

OTHER PUBLICATIONS

PCT Written Opinion PCT/US06/14482, publication date Sep. 25, 2006.
International Search Report PCT/US06/14482, publication date Sep. 25, 2006.

* cited by examiner

*Primary Examiner*—Ahshik Kim
(74) *Attorney, Agent, or Firm*—Neifeld IP Law, PC

(57) ABSTRACT

An apparatus and method for delivering targeted informational messages includes a computer system for creating a de-identified encrypted PID and de-identified patient transaction data in a retail store for transmission and storage. A subset of de-identified encrypted PIDs are associated with targeted informational messages by the system and transmitted to retail stores, where a targeted message is printed on behalf of the patient corresponding to the de-identified encrypted PID.

25 Claims, 8 Drawing Sheets

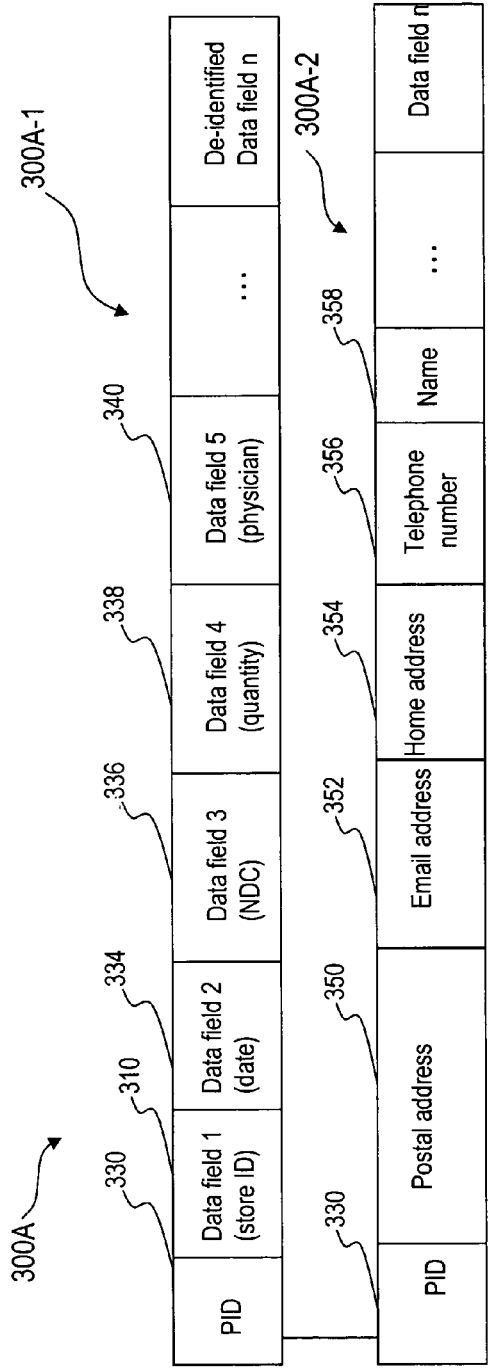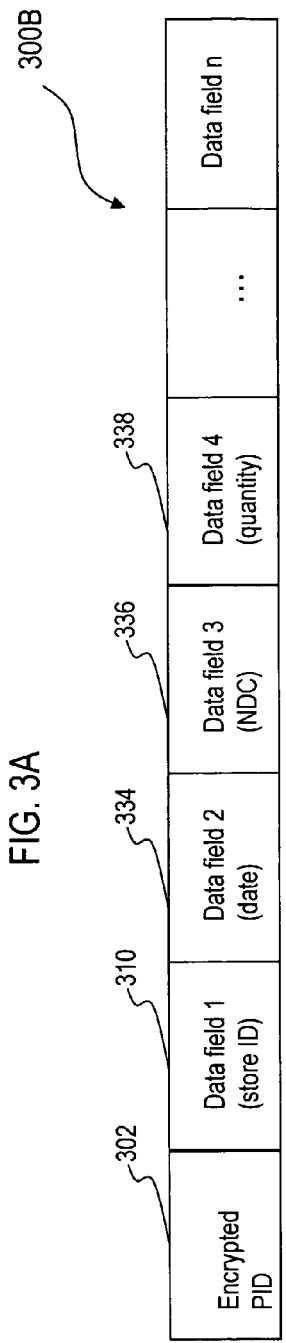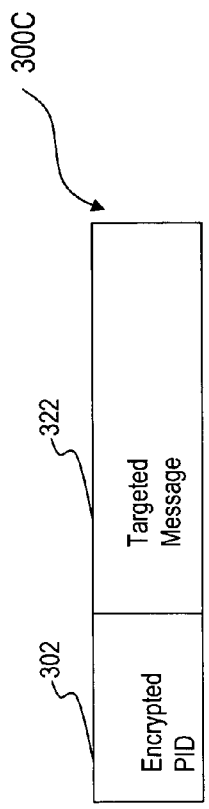
FIG. 3A
FIG. 3B
FIG. 3C

SYSTEM TO PROVIDE SPECIFIC MESSAGES TO PATIENTS

CROSS REFERENCE TO RELATED APPLICATIONS

This application, attorney docket reference PIP 158BANFU-US, claims priority to provisional application 60/685,491 filed May 31, 2005, the contents of which are incorporated herein by reference.

BACKGROUND OF THE INVENTION

1. Field of the Invention

The invention relates to providing specific advisory messages to patients/consumers in a store, pharmacy or other location.

2. Discussion of the Background

U.S. Pat. No. 6,067,524 to Byerly et al. discloses a method and system for generating advisory messages to pharmacy patients. The teachings of U.S. Pat. No. 6,067,524 are incorporated herein by reference.

SUMMARY OF THE INVENTION

Definitions

We refer to a Computer System with the acronym CS.

Certain terms used in this application are defined below. In some cases, examples are provided to clarify the definition.

A consumer, in this application, is synonymous with a patient, or a purchaser of a drug, or one who is prescribed a drug, or one who takes a drug, or one who fills a prescription for a drug or a user of a drug; all of these terms are synonymous with each other.

PID is an acronym for Patient Identification. PID in this application refers to any unique set of symbols that identifies a particular patient. PID is an acronym for "Patient ID." A PID may, for example, be comprised of a sequence of numbers and letters.

POS is an acronym for Point Of Sale. A POS is the area where a consumer engages in transactions at a retail store.

A POS terminal, in this application, means a point of sale terminal, which is an input output device for communicating consumer transaction information between a consumer and a retail store to a CS associated with the retail store.

A POS CS, in this application, means a CS for logging POS transaction data, including any peripheral and input and output devices connected to it, such as POS terminals, optical scanners, printers, etc.

All databases herein may be formatted as one or more files, xml documents, relational database files, and may include tables, forms, queries, relations, reports, modules, and other objects useful in database management and programming. All computers herein may include a digital central processing unit, RAM memory, disk drives, operating system software, and conventional hardware and software to implement, for example, database management and networking.

A product code, in this application, is a code associated with a product. For example, a product code may be a code assigned by a company, a store, or by an industry standard, to a product.

A prescription, in this application, means an order for the preparation and administration of a medicine or drug.

A purchase, in this application, means a transaction involving at least two parties in which forms of payment such as cash, check, charge, debit, smart card, gift card, credit slip, or credit is exchanged for one or more goods or services in a retail store.

Purchase data, in this application, means data associated with purchases. For example, purchase data may include a product code for the product purchased, product description, product purchase list price, actual price paid, date of purchase, time of purchase, transaction ID, location of purchase, discount amount, discount type, and type of payment, and a PID.

A retail store, in this application, refers to a store in which products are located and sold to consumers. Examples of retail stores include pharmacies, supermarkets, quick service restaurants, convenience stores, retail clothing stores, gas stations, petroleum stores, wholesalers, outlet stores, and warehouses.

An individual transaction, in this application, means a single exchange involving at least two legal entities. A purchase is an individual transaction.

Individual transaction data, in this application, means data associated with an individual transaction.

Transaction data, in this application, means data associated with one or more transactions. For example, transaction data may include purchase data, time and date data, PIDs, transaction terminal IDs, store IDs for one or more transactions.

Transaction ID, in this application, refers to a unique identification associated with an individual transaction.

Switch, in this application, refers to a claim adjudication legal entity that accepts individual transaction data from a pharmacy, submits the data to an insurance company reformatted to the data requirements of the insurance company, receives responses thereto from the insurance company, and forwards those responses to the originating pharmacy.

A pharmacy management CS, in this application, refers to a POS CS including a patient database and a drug database that is capable of logging transaction data for consumers in a pharmacy.

A drug database, in this application, refers to a database including at least three of the following: patient names; prescribing history records (e.g., drug, dosage, doctor, date); patient method of payment (e.g., cash, check, credit, or health insurance company); group plan name and member ID; name and address of primary doctor and DEA number of primary doctor; association of prescription to prescribing doctor's ID and contact information; and a drug visualization system to view drug images against actual pills or capsules.

De-identifying patient information means removing sufficient key items from the patient information such that the information cannot be used, alone or in combination with other reasonably available patient information, to identify the individual patient.

Re-identify means to take de-identified patient information and assign it to the identity of the patient.

The SHA-1 Standard defines the Secure Hash Algorithm, SHA-1, for computing a condensed representation of a message or a data file. When a message of any length <264 bits is input, the SHA-1 produces a 160-bit output called a message digest. SHA-1 is described in Federal Information Processing Standards Publication 180-1, Apr. 17, 1995, the entire contents of which are incorporated herein by reference. The SHA-1 is designed to have the following properties: it is computationally infeasible to determine a message which corresponds to a given message digest, or to determine two different messages which produce the same message digest.

The Health Insurance Portability and Accountability Act of 1996 (HIPAA) confirms standards for regulatory approved de-identification. HIPAA approved de-identification requires removal of identifiers for the patient, the patient's relatives, employers, and household members. The test for HIPAA approved de-identification is that "a person with appropriate knowledge of and experience with generally accepted statistical and scientific principles and methods for rendering patient information not individually identifiable" determines that the risk is very small that the patient information could be used, alone or in combination with other reasonably available patient information, to identify a patient and documents the analysis to justify this determination.

HIPAA approved de-identification thus may involve the deletion or alteration of some portion of patient data to protect patient privacy, while preserving the overall statistical and analytical integrity of the data. This is due to the fact that other patient information such as demographics, medical information, and healthcare facility information could be used separately or in combination to discern the identity of some patients.

The safe harbor method for de-identification, in this application, means the method defined by HIPAA. The safe harbor method requires (1) the removal of a list of 18 enumerated patient identifiers and (2) no actual knowledge that the patient information remaining could be used, alone or in combination, to identify the patient. The patient identifiers that must be removed include direct patient identifiers, such as name, street address, social security number, as well as other patient identifiers, such as birth date, admission and discharge dates, and five-digit zip code. The safe harbor method also requires removal of geographic subdivisions smaller than a state, except for the initial three digits of a zip code if the geographic unit formed by combining all zip codes with the same initial three digits contains more than 20,000 people. The safe harbor method does not require the removal of age if less than 90, gender, ethnicity, and other demographic information.

Objects

It is an object of the present invention to provide to patients information that motivates the patients to comply with specified medical treatments and to educate the patient regarding the medications.

It is an object of the present invention to enable pharmacies and other parties (e.g., pharmaceutical companies, consumer goods and grocery manufacturers) to define, develop, and deliver advertising programs targeted at specific groups of patients.

These and other objects are provided by a novel system and method for providing targeted informational messages to individuals, comprising a pharmacy management CS configured to receive individual transaction data and an associated non-encrypted PID, to de-identify the individual transaction data to produce a de-identified individual transaction data, to encrypt said non-encrypted PID to produce an encrypted PID, and to use the encrypted and de-identified data to generate a targeted informational message and deliver that message to the person associated with the PID.

The encryption algorithm produces the same encrypted PID whenever the same un-encrypted PID is input.

The novel system also includes a CS configured to determine from the de-identified transaction data for the transaction associated with the encrypted PID at least one targeted informational message, store the targeted informational message in association with the encrypted PID, and transmit to the POS the targeted informational message in response to receipt of the PID at the POS.

BRIEF DESCRIPTION OF THE DRAWINGS

The invention is described in connection with the following figures, wherein like reference numerals designate identical or corresponding parts.

FIG. 3A shows data structure 300A for database 130A of FIG. 1;

FIG. 3B shows data structure 300B for databases 120A and 130A of FIG. 1;

FIG. 3C shows data structure 300C for databases 120A and 130A of FIG. 1;

DETAILED DESCRIPTION OF THE PREFERRED EMBODIMENTS

Figure 1:
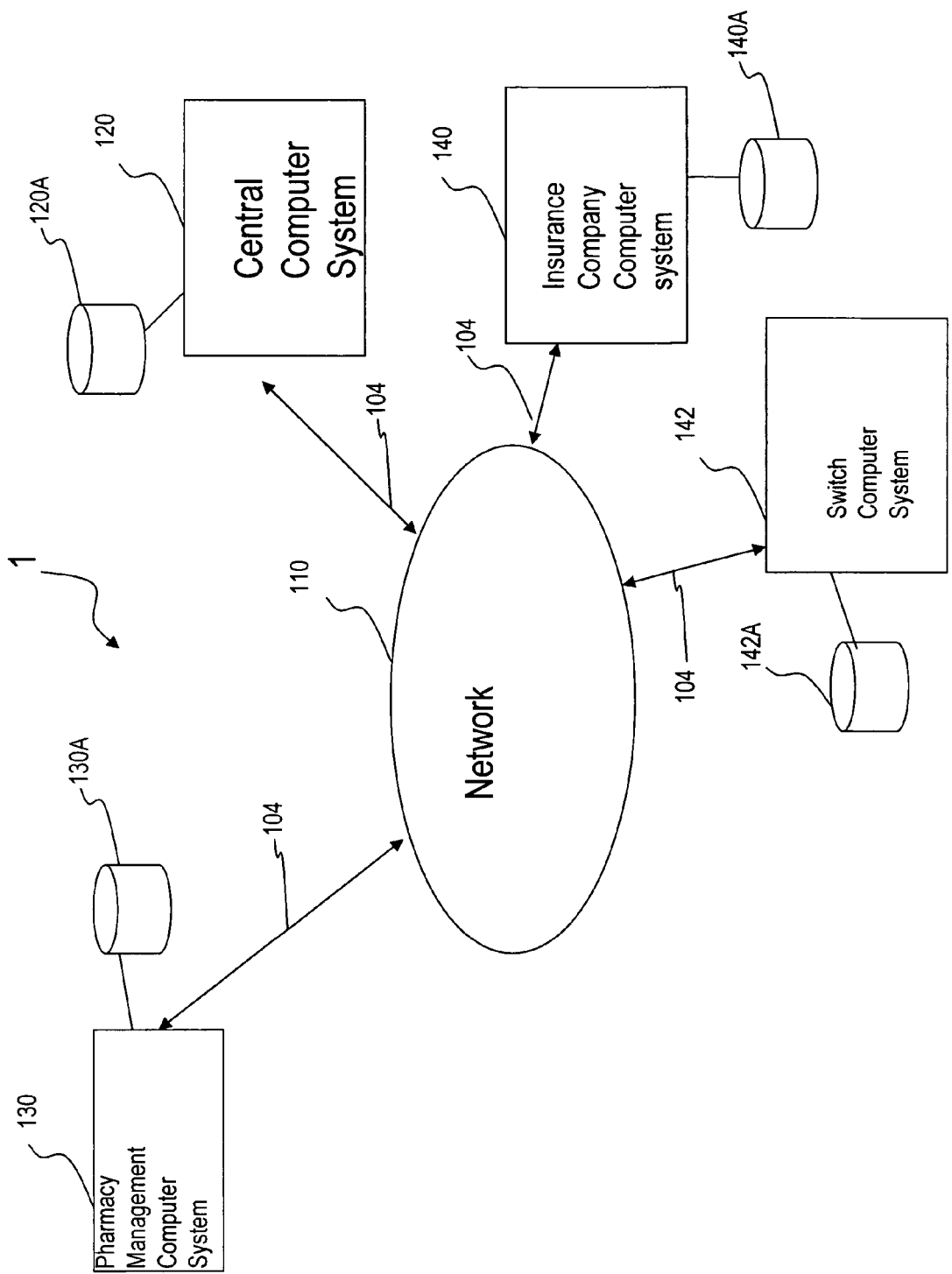
FIG. 1 is a high level schematic diagram illustrating novel system 1.

FIG. 1 shows pharmacy management CS 130, pharmacy management CS database 130A, network 110, communication links 104, central CS 120, central CS database 120A, insurance company CS 140, insurance company CS database 140A, switch CS 142, and switch CS database 142A.

The communication links 104 indicate a means for data transmission including wire and wireless transmission hardware, data format, and transmission protocols. Lines connecting a database to a CS indicates that the computer controls read and write access to that database.

Figure 2:
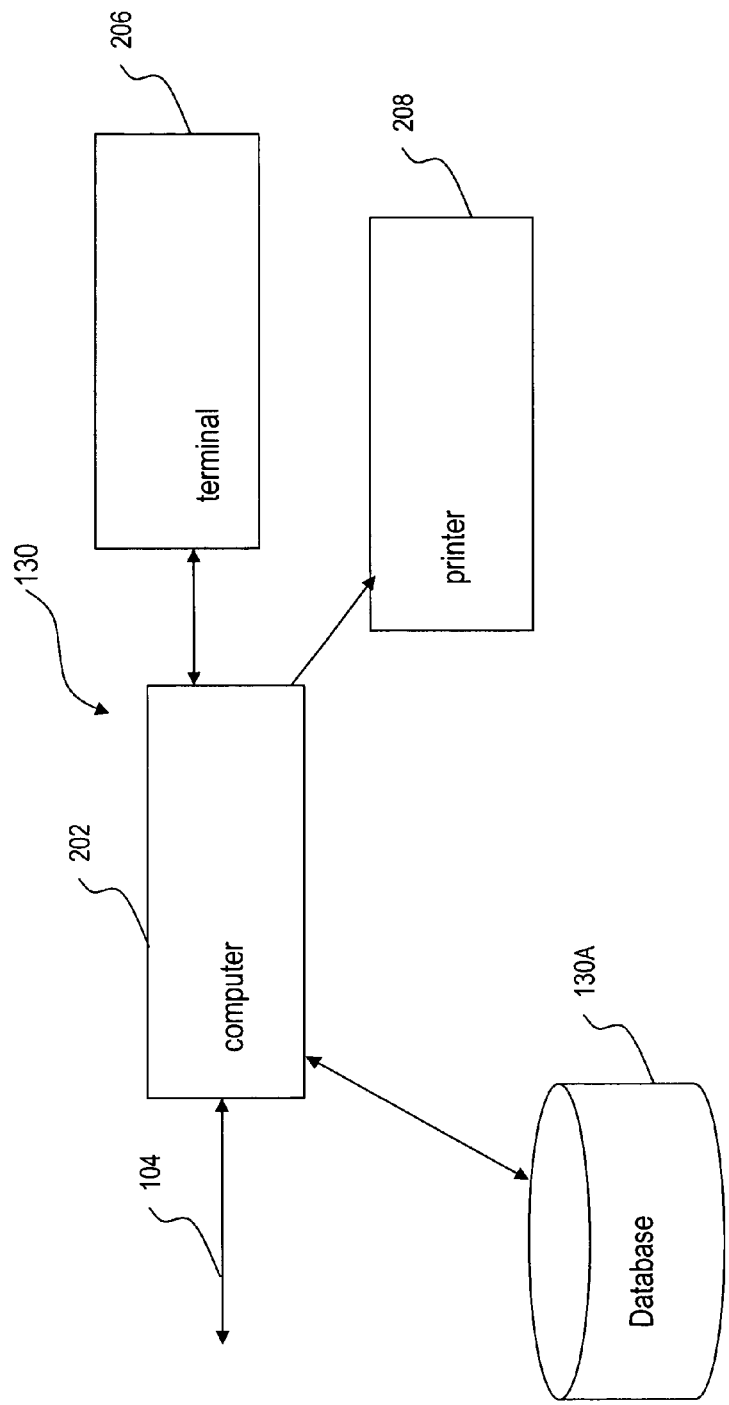
FIG. 2 shows pharmacy management CS 130 of FIG. 1 in more detail.

FIG. 2 shows pharmacy management CS 130 in more detail. FIG. 2 shows computer 202, terminal 206, printer 208, and database server 130A.

FIG. 3A shows data structure 300A including PID table 300A-2 and transaction data table 300A-1. PID table 300A-2 includes data fields associated with a PID that identify the patient, including postal address field 350, email address field 352, name field 358, telephone number field 356 and other data fields that can be used to identify a patient. Transaction table 300A-1 includes data associated with transactions in a pharmacy including PID field 330, store ID field 310, date field 334, NDC field 336, quantity field 338, and physician field 340. Tables 300A-1 and 300A-2 are representative of identification data and transaction data stored in pharmacy management CS 130's database 130A. Data stored in data structure 300B is the result of de-identifying data stored in data structure 300A.

FIG. 3B shows data structure 300B including encrypted PID field 302, and transaction data fields 310, 334, 336, 338, and other non-identifying transaction data fields.

Data structure 300B may be used, for example, as a format for sending de-identified transaction data records from pharmacy management CS 130 to central CS 120. Alternatively, the data structures and functionality described as existing in central CS 120 may reside in the system 130 on the same computer or distributed between computers inside a local area network.

FIG. 3C shows targeted message data structure 300C of central CS 130 associating encrypted PID field 320 and targeted message field 322. Data structure 300C may reside on the CSs 120 and 130. Data structure 300C may be used as a format for transmission of data between systems 120 and 130.

Figure 4:
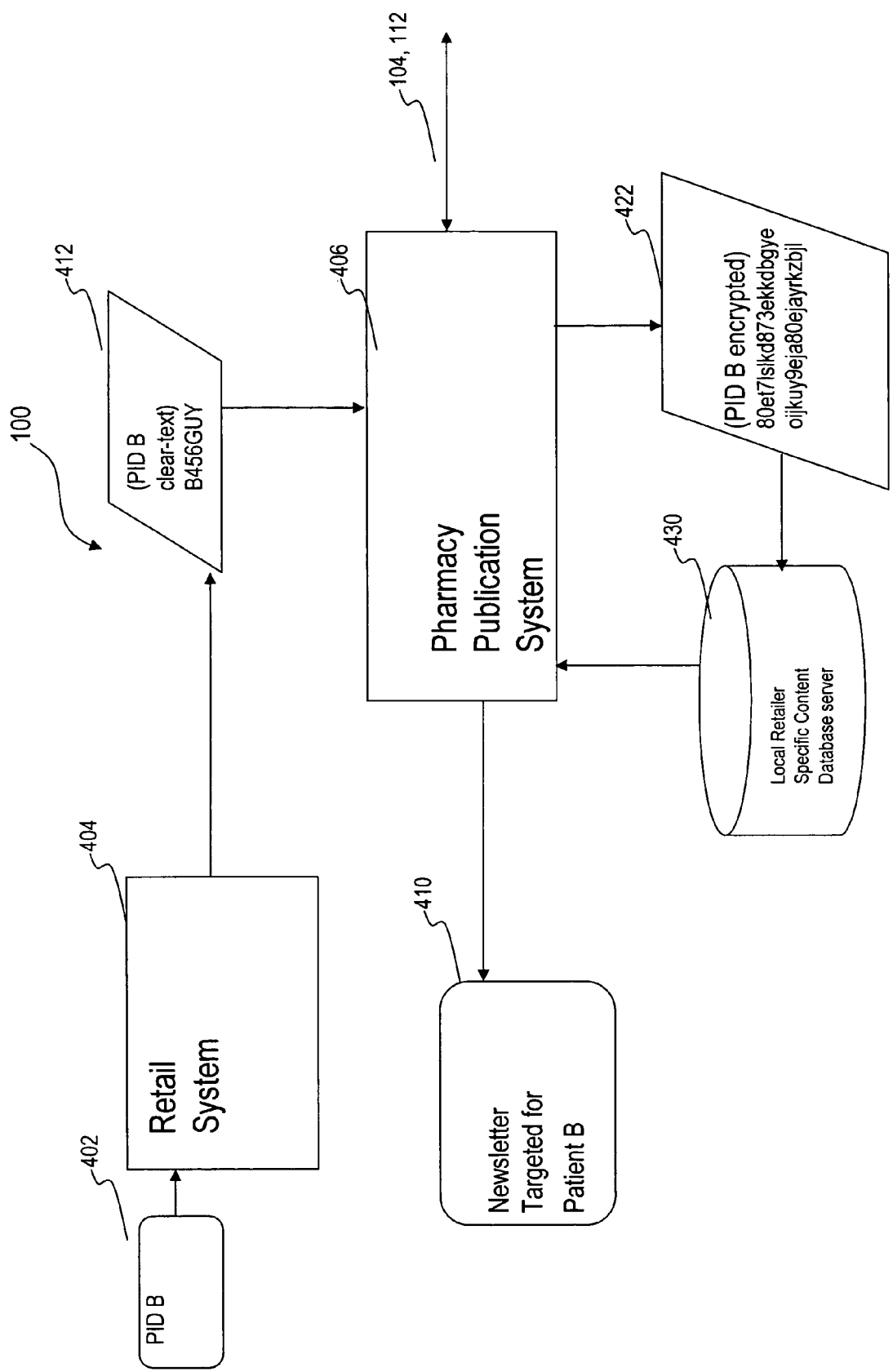
FIG. 4 is a flow diagram showing flow of data in computer equipment associated with one embodiment of system 1 of FIG. 1.
Figure 5:
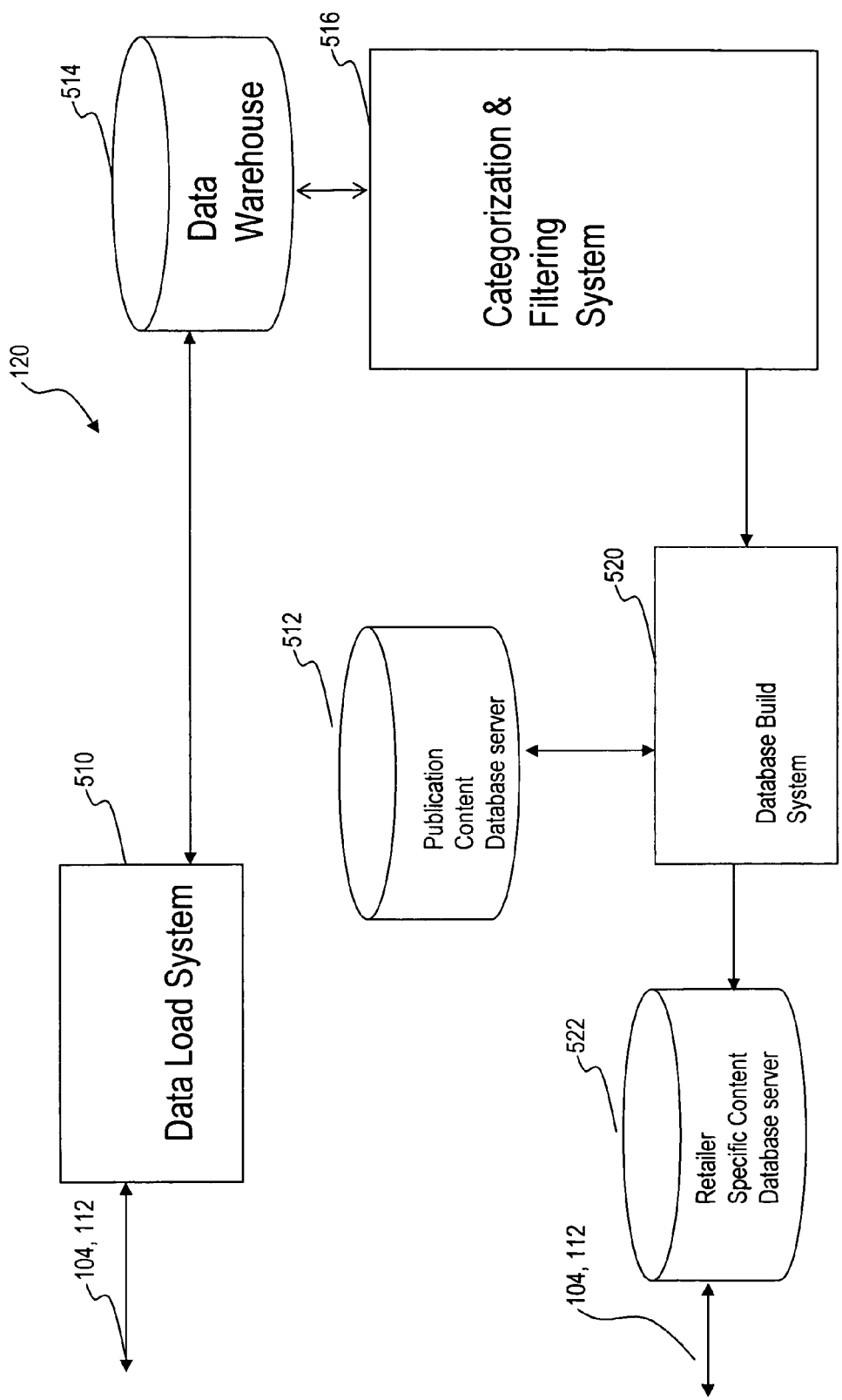
FIG. 5 is a flow diagram showing flow of data in computer equipment associated with one embodiment of either system 120 or system 130 of FIG. 1.
Figure 6:
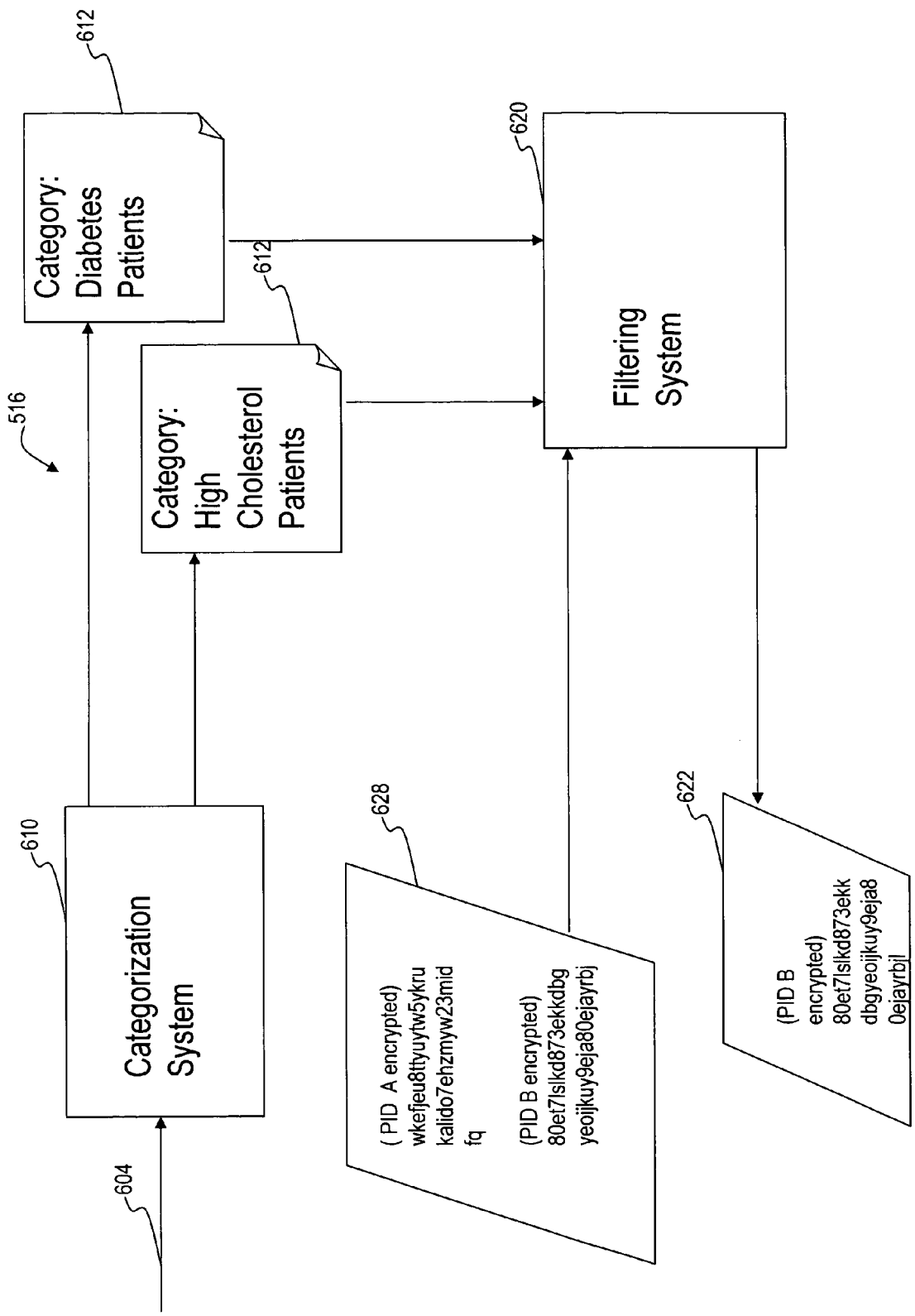
FIG. 6 is a flow diagram showing flow of data in computer equipment associated with element 516 of FIG. 5.

FIGS. 4-6 diagram flow of data in a specific embodiment or closely related embodiments.

FIG. 4 is a flow diagram showing the flow of data in pharmacy management CS 130. FIG. 4 shows retail system 404, pharmacy publication system 406, and local retailer specific content database server 430. FIG. 4 also shows generating for PID B targeted newsletter at 410 which is an output of pharmacy publication system 406. FIG. 4 also shows receipt of input into retail system 404 of PID B, at 402. FIG. 4 also shows transmission of clear-text (unencrypted) patient data and encrypted patient data 422 from retail system 404 to pharmacy publication system 406 of 412.

In exemplary embodiments of the present invention, retail system 404, retailer specific database 330, and pharmacy publication system 406 may be structured as sub-systems of a single CS, or, alternately, may be structured as a physically distributed CS comprising separate computers interconnected by conventional communication hardware and software.

Retail system 404 includes a digital CS and a local data server, which may be a POS CS or a pharmacy management CS. Pharmacy data may be stored locally in databases located on a data server at the corresponding pharmacy.

Pharmacy management CS 130 may be coupled to a distinct POS CS to enable the passing of pricing information between the pharmacy management CS 130 and the distinct POS CS. This information may include pharmacy product identification, price, amount, and bar code identification. A corresponding bar code printed on a label of a prescription or product enables both CSs to identify product pricing for transactions at a POS of either CS.

Pharmacy publication system 406 includes a digital CS including a printer, and a local data server. Pharmacy publication system 406 also includes hardware or software for implementing encryption algorithms, for example the SHA-1 algorithm.

Local retailer specific content database server 430 stores the encrypted PIDs and associated targeted messages, such as data in data structure 300C. It may also store the unencrypted identifiable data such as in data structure 300A and the encrypted de-identified individual transaction data such as in data structure 300B. Pharmacy publication system 406 also functions to transmit to central CS 120 via link 104 de-identified encrypted data records corresponding to individual transactions in the corresponding pharmacy. Pharmacy publication system 406 also functions to receive data records via link 104 from central CS 120 having encrypted PIDs and targeted messages such as in the form of data structure 300C and to store those records in database 430.

In operation, retail system 404 receives an unencrypted PID from patient B and transmits patient B's unencrypted PID B and patient B's individual transaction data to pharmacy publication system 406.

Next, pharmacy publication system 406 applies the SHA-1 algorithm to the patient B's unencrypted PID B to produce patient B's encrypted PID B and applies de-identification computer code to generate associated de-identified individual transaction data.

Pharmacy publication system 406 transmits patient B's de-identified transaction data and patient B's encrypted PID to data load system 510 via local link 112 or network link 104.

During a transaction in the pharmacy involving a PID, pharmacy publication system 406 queries database 430 for targeted messages corresponding to that PID. Pharmacy publication system 406 may store a look-up table corresponding to each PID an associated encrypted PID, or it may determine during each transaction the encrypted PID from the received PID, and then determine whether the encrypted PID has a targeted message.

Pharmacy publication system 406 may then retrieve and print any targeted messages for that PID immediately in real time, for example, during the transaction in which the PID was received or while the patient is at the retail store or pharmacy of systems 430, 404. Pharmacy publication system 406 may also, for example, print any retrieved targeted messages as an attachment to a prescription label, as a newsletter 310 on a separate paper, or as an attachment to a transaction receipt.

Any secure one-way algorithmic encryption process or encrypting hash algorithm that takes a unique unencrypted sequence of symbols (e.g., numbers or letters) as input and produces a unique encrypted sequence of symbols as output, such that the same unique encrypted output is produced for a given unique input, may be used as an alternative to the SHA-1 algorithm.

FIG. 5 is a flow diagram showing the flow of data preferably in central CS 120, or alternatively in pharmacy management CS 130. FIG. 5 shows data load system 510, data warehouse 514, categorization and filtering system 516, database build system 520, publication content database server 512, and retailer specific content database server 522.

In exemplary embodiments, data load system 510, data warehouse 514, categorization and filtering system 516, database build system 520, publication content database server 512, and retailer specific content database server 522 may be structured as sub-systems all residing within a single computer, or, alternatively, may be structured as a physically distributed CS interconnected by conventional communication hardware and software.

In operation, data load system 510 receives as input SHA-1 encrypted PIDs linked to de-identified transaction data from pharmacy publication system 406 via data network link 104 or local data link 112. Data load system 510 transforms de-identified patient data into a structure consistent with the data warehouse 514 requirements. Data load system 510 then outputs de-identified patient data including an SHA-1 encrypted PID to data warehouse 514. Data load system 510 may, for example, populate tables in the data warehouse schema and then verify that the data is ready for use. Data load system 510 may, for example, verify the referential integrity between tables to ensure that all records relate to appropriate records in other tables.

In operation, data warehouse 514 functions, for example, as a data repository for organizing, structuring and storing plural pharmacies' individual transaction data for query and analysis. Data warehouse 514 implements a process by which large quantities of related data from many operational systems is merged into a single, standard repository to provide an integrated information view based on logical queries. For example, data warehouse 514 may be a repository of 65 weeks of individual transaction data from 12,500 retail stores including therein a large number that either are pharmacies or include therein pharmacies, and store therein de-identified historical patient profiles.

Types of logical queries may relate to "data mining," which can be defined as a process of data selection, exploration and building models using vast data stores to uncover previously unknown patterns. Other queries may be in support of research on a particular subject. In operation, data warehouse 514 serves as a tool that can provide information for use in a wide variety of therapeutic, statistical, and economic analyses and interventions to aid in making healthcare and business related decisions. In operation, data warehouse 514 can also generate and store feedback regarding the impact of prior decisions, facilitating improvements in patient care, operational efficiency, and reducing the cost of medical care.

In operation, categorization and filtering system 516 formulates and executes DBMS (Data Base Management System) queries on the de-identified individual transaction data residing on data warehouse 514, using for example, SQL boolean logic and filtering operations. Categorization and filtering system 516 filters the query results to produce a subset of encrypted PIDs linked to de-identified individual transaction data matching categorization and filtering criteria. If the de-identified individual transaction data for one or more transactions linked to an encrypted PID matches certain categorization and filtering criteria, then the linked encrypted PID is termed a qualified encrypted PID. Categorization and filtering system 516 outputs a certain set of qualified encrypted PIDs to database build system 520.

In operation, categorization and filtering system 516 may implement DBMS selection operations based upon complex criteria. These operations may be implemented as a series of simple queries using, for example, relatively simple SQL boolean logic, selection, and filtering operations. Such a series of simple queries may result, for example, in a series of intermediate tables or work tables that are progressively more refined and contain progressively smaller subsets of qualifying records. Partitioning the query tasks of categorization and filtering system 516 in this way may result in increased database access efficiency and shorter processing times. Partitioning the categorization and filtering operation into a series of simple query operations also promotes ease of programming, maintenance, modification, and testing.

In operation, database build system 520 receives as input from categorization and filtering system 516 a certain set of qualified encrypted PIDs. Database build system 520 queries publication content database server 512 for targeted messages associated with that certain categorization and filtering criteria. The retrieved targeted messages are those associated with the certain categorization and filtering criteria used to produce the certain set of qualified encrypted PIDs. Database build system 520 associates the retrieved targeted messages with the set of encrypted PIDs, for example, by combining the qualified encrypted PIDs output from categorization and filtering system 516 with the certain targeted messages retrieved from publication content database server 512. Database build system 520 outputs targeted messages linked to qualified encrypted PIDs to retailer specific content database server 522. Preferably, the output also associates store ID or retailer ID with the encrypted PID. Database build system 520 may, for example, create and populate tables of targeted messages linked to qualified encrypted PIDs on retailer specific content database server 522.

In operation, publication content database server 512 services queries from database build system 520 for targeted messages.

In operation, retailer specific content database server 522 receives as input updates of retailer specific targeted newsletter content from database build system 520. Retailer specific content database server 522 functions to provide updated retailer specific targeted newsletter content to pharmacy publication system 406 via data links 104 and 112 and network 110 using, for example, File Transfer Protocol (FTP).

In exemplary embodiments, the functions of central CS 120 necessary to generate advisory messages associated with encrypted PIDs may be performed by suitably configured embodiments of pharmacy management CS 130.

FIG. 6 is a flow diagram showing the flow of data in categorization and filtering system 516. FIG. 6 shows categorization system 610 and filtering system 620. In exemplary embodiments, categorization system 610 and filtering system 620 may be structured as sub-systems all residing within a single computer, or, alternately, may be structured as a physically distributed CS interconnected by conventional communication hardware and software.

FIG. 6 also shows categories 612 which are outputs of categorization system 610 and inputs to filtering system 620. FIG. 6 also shows de-identified patient data output 628 of data warehouse 514 as input to filtering system 620. FIG. 6 also shows filtering system 620 outputting filtered de-identified patient data 622.

Figure 7:
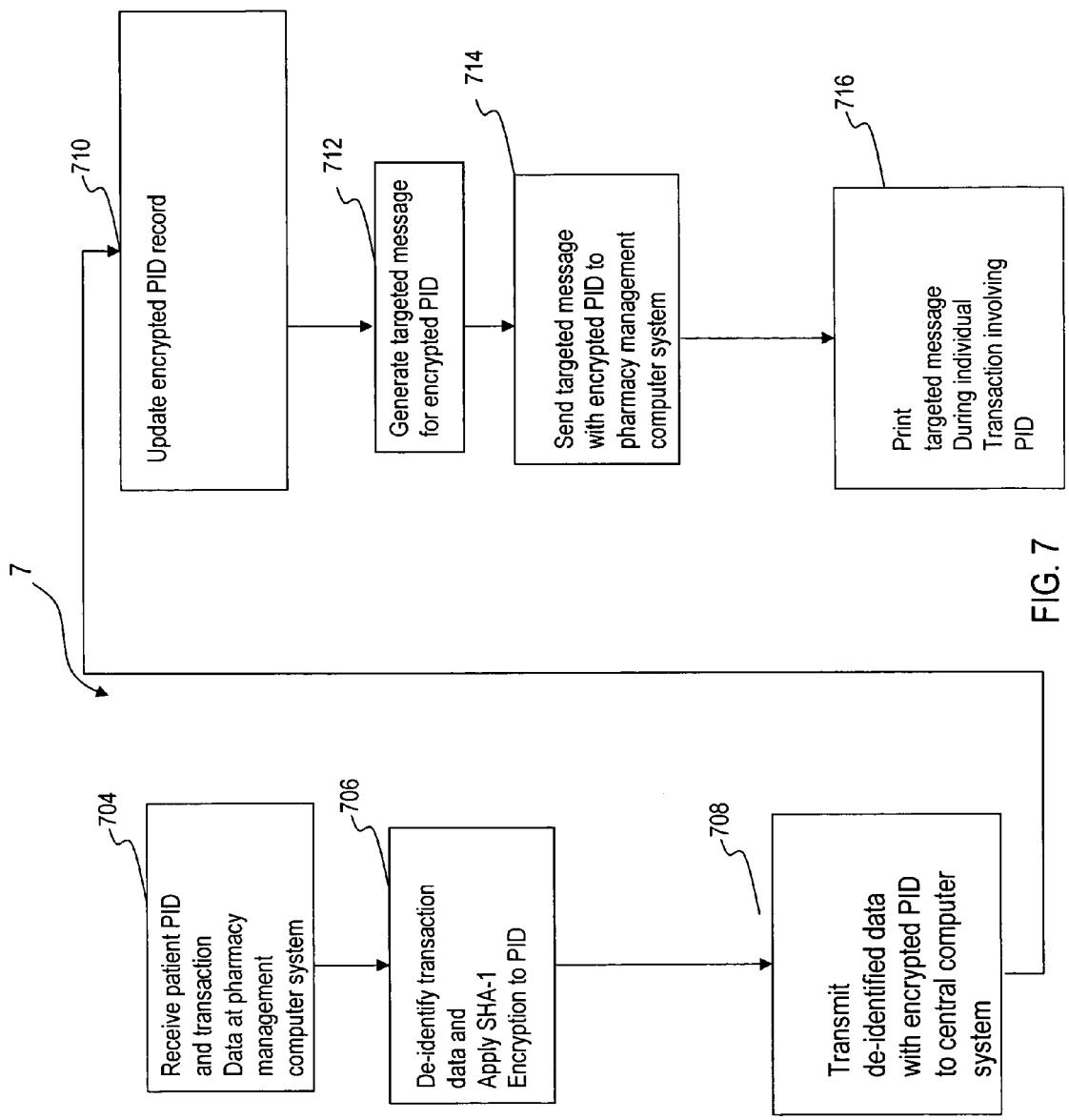
FIG. 7 is a flow chart of a method of the invention.

FIG. 7 shows a flowchart depicting a method for operating system 1.

In step 704, patient PID and transaction data are received at pharmacy management CS 130. For example, the patient's name may be input at retail system 404 and the patient's PID then retrieved from a database.

In step 706, pharmacy management CS 130 encrypts the PID and de-identifies the individual transaction data.

In step 708, pharmacy management CS 130 transmits de-identified transaction data linked to encrypted patient PID 422 to central CS 120.

In step 710, the central CS 120 updates its data store of individual transaction data records associated with the encrypted PID by adding the newly received individual transaction data thereto.

In step 712, central CS 120 matches the encrypted PID with a targeted message using the encrypted PID as the search key.

For example, central CS 120 identifies a safety warning relating to a drug previously purchased by the patient having the encrypted PID, and associates that warning with the encrypted PID.

For another example, central CS 120 identifies a brand of a first drug previously purchased by the patient associated with the encrypted PID and associates with the encrypted PID marketing material for a different brand of the same drug or a brand of a different drug used for the same clinical indication as the first drug with the encrypted PID.

For another example, the central CS 120 identifies lack of purchase in a pattern of prior purchases of a first drug or drugs having the same clinical indication as the first drug and associates with the encrypted PID a targeted message identifying at least one brand of a drug or drugs having that clinical indication.

In step 714, central CS 120 transmits a targeted message with an encrypted PID to pharmacy management CS 130.

In step 716, pharmacy management CS 130 prints targeted newsletter 410 in response to the receipt of the PID corresponding to the encrypted PID or in response to a transaction including that PID.

Figure 8:
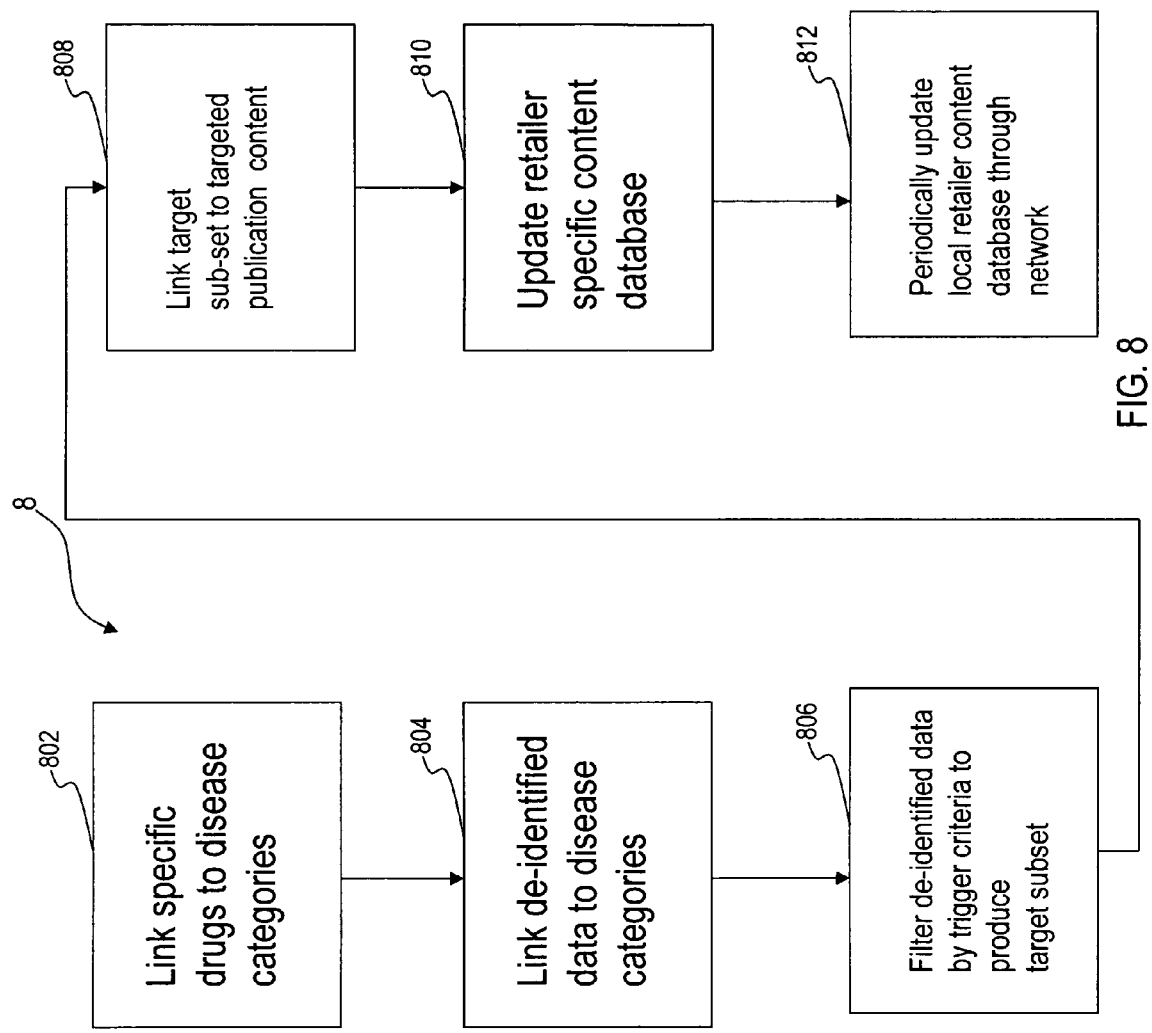
FIG. 8 is a flow chart of a method of the invention.

FIG. 8 shows a method of using system 120.

In step 802, categorization system and filtering system 516 links specific drugs to specific disease categories. For example, the drug Lipitor is associated with the disease category "high cholesterol patients" and the drug insulin is associated with associated with the disease category "diabetes patients."

In step 804, categorization system and filtering system 516 links de-identified data in data warehouse 514 to specific disease categories. For example, if a de-identified data record indicates that insulin has been purchased in the past, then that de-identified data record is allocated to the category "diabetes patients."

In step 806, categorization system and filtering system 516 further filters the de-identified data records allocated to patient categories created in step 804 to produce targeted subsets. For example, system 516 creates one subset for "high cholesterol patients" and one subset for "diabetes patients," or subsets for patients in both categories or only one of each category. For example, the operations of step 806 may be implemented as a series of DBMS queries using, for example, SQL boolean logic, selection, and filtering operations. Such a series of simple queries may result, for example, in a series of intermediate, or work, tables, that are progressively more refined and contain progressively smaller subsets of qualifying de-identified data records.

In step 808, database build system 520 links the targeted de-identified data record subsets produced in step 806 with appropriate targeted messages from publication content database server 512 where, for example, one targeted message for patients of both categories and one each for patients having only one of diabetes and high cholesterol. For example, database build system 520 may extract the encrypted PID from a de-identified data record and link the encrypted PID to an appropriate targeted publication.

In step 810, database build system 520 updates retailer specific content database server 522 with targeted publications data linked to encrypted PIDs, and the store IDs with which the encrypted PIDs are each associated.

Exemplary embodiments may target for an informational communication for example the following subsets of de-identified patients (A)-(N):

A) Patients on two or more medication that clarify the exact disease for which they are being treated that a single medication does not properly identify.

B) Patients taking two or more medications over time indicating their disease is requiring additional treatment to maintain or control its progression.

C) Patients taking a sequence of drugs indicating what stage of therapy within the patient's disease, patient currently is in.

D) Patients not currently being treated for a particular condition but who are likely candidates for drug therapy due to one or more risk factors as defined by other medications within the patients drug profile.

E) Patients who are already compliant and or persistent on their medication regimen as defined by consistent use of drug therapy over time.

F) Patients who have already switched from one medication within a drug class to another medication within same or different drug class known to treat the same condition.

G) Patients who are using medications for chronic treatment vs. acute treatment for a particular disease by identifying patients receiving multiple new prescriptions for the same drug over time.

H) Patients that should be eliminated from a patient subset due to a known drug contraindication as identified by additional drug therapy creating the contraindication.

I) Patients that should be eliminated from a patient subset due to a known drug interaction as identified by additional drug therapy creating the drug interaction.

J) Patients that have stopped taking their current medication as identified by being late for a prescription refill and reminding them to continue their therapy.

K) Patients that have stopped taking their current medication as identified by being late for a prescription refill and inform them of other medications used to treat the same condition that may work better for them.

L) Patients who have previously used medications to treat seasonal conditions that could benefit from similar medication therapy upon the next seasonal event.

M) Patients who may be taking two drugs in combination that could benefit from taking one drug containing both individual drug ingredients.

N) Patients who may benefit from a refill reminder just prior to their prescription refill due date as identified by previous non-compliant prescription refill behavior.

In addition, the present invention may trigger the production of informational messages based on the following exemplary selection or filtering criteria: age under 90; gender; payer identification; cash payment; NDC; pill count; number of refills; refills remaining on the prescription; new or refill prescription; BIN (Bank Identification Number); NCPDP (National Council for Prescription Drug Programs) provider ID, which is an (individual pharmacy identifier; and DEA (Drug Enforcement Administration) number (encrypted).

For example, using embodiments of the present invention, a selection or filtering program can be designed to reach a patient population undergoing a specific drug treatment protocol and which falls within desired (specified) demographic and insurance parameters.

The present invention enables additional segmentation and targeting by using, for example, a unique pharmacy outlet identifier (pharmacy or store ID) and its geographic location as a proxy for a patient's home address.

Using these targeted message criteria (also referred to as trigger criteria and as categorization and filtering criteria) in exemplary embodiments allows the delivery of variable and highly relevant information to a large number of different patient groups. The present invention thereby provides sophisticated patient service functionality by targeting highly relevant informational messages at specific groups of patients.

With the present invention, it is not required that all pharmacies provide targeted messages resulting from any or all trigger criteria. Each pharmacy or store or set of stores commonly owned may select to implement criteria of their choosing, for example, by marketing category, by manufacturer, or as a regulatory required message.

An advantage of the present invention is that the types of selection programs created reflect the drug information data available at any given moment in time.

Systems 120, 130 may collect and maintain a set of logs, which may contain, for example, accounting information related to newsletter production. These logs, for example, may be used to support billing functions and may also be used in troubleshooting. The logs may be processed and loaded by data load system 510 and may reside on data warehouse 514, for example.

The following de-identified data, for example, may be captured by the system of the present invention in logs: prescription number; NDC (National Drug Code); age under 90; gender; pill count; refill number; new or refill; and refills remaining.

Logs may be transmitted to central CS 120 daily, for example, overnight, and then may, for example, be maintained by central CS 120 for a period of time (for example, 1 year) before being purged or may be maintained indefinitely.

Log data preferably is de-identified and maintained secure from unauthorized access. Log data can be aggregated to assess effectiveness rates for the advertising programs.

The inventors conceive of changes, for example, to the triggering, newsletter printing, and data logging processes, as needed.

In an embodiment, pharmacy management CS 130 combines a PID with a pharmacy chain ID, a store ID and optionally a transaction ID to form a combination ID. The combination ID may be associated with the PID or the encrypted PID.

A third party's CS may hash a vendor specific value (using, for example, the SHA-1 algorithm) into PIDs used in that vendor's retail store. This encrypted data may then be maintained outside of the control of the user of the central system 120, for additional security.

The present invention advantageously allows HIPAA acceptable reduced logging of pharmacy data in locations where population size is below 20,000 for a 3-digit zip code and allows for the handling the age of patients 90 years old and above as 90 years old.

Embodiments recognize that since a store location can serve as a reasonable proxy for a 5 digit zip code, that in the sparsely populated areas that fall into this category the correlation is likely higher. Logging may therefore depend on zip code and assorted population sizes of store geographic locations. Central CS 120 may, for example, aggregate transaction data for all (presently 17) restricted 3 digit zip codes into a single 3 digit zone 000.

Alternatively, for areas having small populations, PID information may not be transmitted out of the corresponding pharmacy stores and information logged in any CS may exclude PID information. In these alternatives, no informational messages are targeted based upon prior transaction history of an individual. Instead, information may be triggered in the pharmacy management CS by NDC, age, gender, or the like, although age and gender may not be logged.

Embodiments may use time intervals between prescription filling dates as a surrogate for actual date data. This alternative provides the ability to perform the desired analytics and correlations while minimizing the risk of re-identification. The time interval may be supplied by pharmacy management CS 130. Alternatively, central CS 120's software may calculate the time interval before writing information to logs.

Embodiments may advantageously use data from physician offices to provide, for example, helpful compliance dates (specifically around first fill rates).

Embodiments may advantageously link pharmacy and physician office data to allow maximal de-identified compliance solutions.

Embodiments may advantageously allow the addition of outside information model components in a compliant de-identified method.

Embodiments may advantageously allow the handling large-scale, multi-source, patient-level information.

Embodiments may advantageously aggregate de-identified patient data to develop additional service offerings.

The PID may be credit card numbers, pharmacy or health related identification numbers, and any other identification used by a patient.

With the present invention, there is no way for an unauthorized third party to determine a card holder's real identity even if central CS 120's security is compromised. However, the present invention can still target the card holder for targeted informational messages because every time the retail store sees the customer's card number that number may be associated with the customer's transaction data already stored in association with some unique encrypted PID.

Typically, credit card transactions to pay for pharmacy purchases and corresponding pharmacy prescription order transactions are separate data transactions, in the sense that the information transmitted from the pharmacy management CS in association with the credit card identifier does not contain product or service purchase information. Moreover, in preferred embodiments, purchase of non pharmacy goods, such as purchases from a supermarket and corresponding credit card identifier or other personal identifier are stored in association with at least part of the credit card identifier or other personal identifier in one data structure, whereas purchases of pharmacy prescription products, are stored in separate data structures having no association between any identifiers in the two separate data structures. The inventors do conceive of, as a currently non-preferred embodiment, the de-identification and ID encryption process employable for both non pharmacy retail store POS transactions and pharmacy transactions. In such an embodiment, both non-pharmacy and pharmacy transactions for transaction inside of one retail store or in one retail store chain, may be associated with one another, and still effectively maintain pharmacy patient anonymity.

Some embodiments shown in the figures illustrate a division of processing among separate units or machines. This is not a requirement of the invention, and the various elements could be combined into fewer machines, be distributed among various machines differently, or, in fact, be contained in a single machine with a single computer. Embodiments utilizing such redistributions can be designed by practitioners in the relevant arts.

What is claimed is:

1. A system for providing targeted informational messages to individuals, comprising:
 a pharmacy management computer system configured to:
 (a) receive individual transaction data and an associated non-encrypted PID from a terminal for an individual transaction including a prescription;
 (b) de-identify said individual transaction data to produce de-identified individual transaction data;
 (c) encrypt said non-encrypted PID to produce an encrypted PID);
 (d) store at least one targeted informational message in association with said encrypted PID;
 (e) in response to receipt by said pharmacy management computer system of said PID during a subsequent individual transaction at a certain terminal, transmit to said certain terminal said at least one targeted informational message; and further comprising a central computer system; and wherein said pharmacy management computer system is configured to transmit said de-identified individual transaction data in association with said encrypted PID for said individual transaction to said central computer system.

2. The system of claim 1, wherein said pharmacy management computer system is configured to de-identify said transaction data by removing from said transaction data at least one of the following items: name, street address, social security number, birth date, admission date, discharge dates, five-digit zip code, and geographic subdivision smaller than a state of the United States.

3. The system of claim 1, wherein said pharmacy management computer system is configured to de-identify said transaction data by removing from said transaction data all of the following items: name, street address, social security number, birth date, admission date, discharge dates, five-digit zip code, and geographic subdivision smaller than a state.

4. The system of claim 1, wherein said non-encrypted PID is encrypted using a SHA-1 Secure Hash Algorithm.

5. The system of claim 1, further comprising a printer at said certain terminal and wherein said pharmacy management computer system is configured to instruct said printer to print said targeted informational message.

6. The system of claim 1, wherein said central computer system is configured to store said encrypted PID and said de-identified individual transaction data in association with records for prior transactions associated with said encrypted PID.

7. The system of claim 6, wherein said central computer system is configured to apply certain targeting criteria to de-identified transaction data associated with said encrypted PID.

8. The system of claim 7, wherein said central computer system is configured to associate with said encrypted PID a certain targeted message associated with said certain targeting criteria when said de-identified transaction data associated with said encrypted PD meets said certain targeting criteria.

9. The system of claim 8, wherein said central computer system is configured to transmit to pharmacy management computer system said certain targeted message in association with said encrypted PID.

10. The system of claim 9, wherein said pharmacy management computer system is configured to store said certain targeted message in association with either said encrypted PID or said PID.

11. The system of claim 1, wherein said pharmacy management computer system is configured to de-identify said transaction data by removing from said transaction data at least one of the following items: name, street address, social security number, birth date, admission date, discharge dates, five-digit zip code, and geographic subdivision smaller than a state of the United States; and
   wherein said individual transaction data includes at least one of store ID and quantity.

12. The system of claim 1, wherein said pharmacy management computer system is configured to de-identify said transaction data by removing from said transaction data at least one of admission date, discharge dates, and zip code;
   wherein said individual transaction data includes at least one of store ID and quantity.

13. A computer implemented method for providing targeted informational messages to individuals, comprising:
   (a) receiving in a pharmacy management computer system individual transaction data and an associated non-encrypted PID from a terminal for an individual transaction including a prescription;
   (b) de-identifying in said pharmacy management computer system said individual transaction data to produce de-identified individual transaction data;
   (c) encrypting in said pharmacy management computer system said non-encrypted PID to produce an encrypted PID;
   (d) storing at least one targeted informational message in association with said encrypted PID;
   (e) in response to receipt by said pharmacy management computer system of said PID during a subsequent individual transaction at a certain terminal, transmitting to said certain terminal said at least one targeted informational message; and
   further comprising transmitting from said pharmacy management computer system said de-identified individual transaction data in association with said encrypted PID for said individual transaction to said central computer system.

14. The method of claim 13, wherein said de-identifying in said pharmacy management computer system comprises removing from said transaction data at least one of the following items: name, street address, social security number, birth date, admission date, discharge dates, five-digit zip code, and geographic subdivision smaller than a state.

15. The method of claim 13, wherein said de-identifying in said pharmacy management computer system comprises removing from said transaction data all of the following items: name, street address, social security number, birth date, admission date, discharge dates, five-digit zip code, and geographic subdivision smaller than a state of the United States.

16. The method of claim 13, wherein said encrypting in said pharmacy management computer system comprises using a SHA-1 Secure Hash Algorithm.

17. The method of claim 13, further comprising instructing a printer at said certain terminal to print said targeted informational message.

18. The method of claim 13, further comprising storing in said pharmacy management computer system said encrypted PID and said de-identified individual transaction data in association with records for prior transactions associated with said encrypted PID.

19. The method of claim 18, further comprising said pharmacy management computer system applying certain targeting criteria to de-identified transaction data associated with said encrypted PID.

20. The method of claim 19, further comprising said pharmacy management computer system associating with said encrypted PID a certain targeted message associated with said certain targeting criteria when said de-identified transaction data associated with said encrypted PID meets said certain targeting criteria.

21. The method of claim 20, further comprising transmitting from set central computer system to pharmacy management computer system said certain targeted message in association with said encrypted PID.

22. The method of claim 21, further comprising storing in said pharmacy management computer system said certain targeted message in association with either said encrypted PID or said PID.

23. The method of claim 13, wherein step (e) comprises transmitting said encrypted PID and said at least one targeted informational message from said central computer system to said pharmacy management computer system and to said certain terminal during said subsequent individual transaction.

24. The method of claim 13, wherein said de-identifying in said pharmacy management computer system comprises removing from said transaction data at least one of the following items: name, street address, social security number, birth date, admission date, discharge dates, five-digit zip code, and geographic subdivision smaller than a state; and wherein said individual transaction data includes at least one of store ID and quantity.

25. The system of claim 13, wherein said pharmacy management computer system is configured to de-identify said transaction data by removing from said transaction data at least one of admission date, discharge dates, and zip code;

wherein said individual transaction data includes at least one of store ID and quantity.

* * * * *